(12) United States Patent
Laitinen-Vellonen (10) Patent No.: US 7,108,774 B1
(45) Date of Patent: Sep. 19, 2006

(54) METHOD FOR ANALYZING A PAPERMAKING PROCESS AND AN ELECTROCHEMICAL SENSOR FOR ANALYZING LIQUID

(75) Inventor: Sakari Laitinen-Vellonen, Jyskä (FI)

(73) Assignee: Liqum Oy, Jyvaskyla (FI)

( * ) Notice: Subject to any disclaimer, the term of this patent is extended or adjusted under 35 U.S.C. 154(b) by 455 days.

(21) Appl. No.: 10/089,985

(22) PCT Filed: Oct. 6, 2000

(86) PCT No.: PCT/FI00/00861

§ 371 (c)(1),
(2), (4) Date: Apr. 3, 2002

(87) PCT Pub. No.: WO01/25774

PCT Pub. Date: Apr. 12, 2001

(30) Foreign Application Priority Data

Oct. 6, 1999 (FI) .................................. 19992158
Jan. 20, 2000 (FI) .................................. 20000111

(51) Int. Cl.
*G01N 27/27* (2006.01)
*G01N 27/403* (2006.01)

(52) U.S. Cl. ................... 204/409; 204/406; 204/411
(58) Field of Classification Search ............... 204/406, 204/409, 411
See application file for complete search history.

(56) References Cited

U.S. PATENT DOCUMENTS 3,616,272 A * 10/1971 Goerg et al. ............. 205/787.5
3,676,321 A * 7/1972 Cummings et al. ......... 204/406
3,957,592 A    5/1976 Young
4,605,900 A    8/1986 Moilanen et al.
4,655,880 A * 4/1987 Liu ........................ 205/777.5
4,818,348 A    4/1989 Stetter
4,933,292 A    6/1990 Savisalo et al.
5,074,157 A   12/1991 Marsoner et al.
5,120,421 A * 6/1992 Glass et al. ................. 204/406
5,503,720 A * 4/1996 Teske ......................... 205/787
5,916,522 A    6/1999 Boyd et al.

FOREIGN PATENT DOCUMENTS

WO    9522051    8/1995
WO    9705476    2/1997

OTHER PUBLICATIONS

Winquist et al, Meas. Sci. Technol., 9, pp. 1937-1946, 1998.*
Toxic Gas CiTiceLS, manual from City Technology Ltd, published on or before Jul. 30, 1999, pp. 2-39.*
Di Natale C. et al. "Multicomponent analysis on polluted waters by means of an electronic tongue". Oct. 1997, Elsevier, Switzerland; pp. 423-428.
Mitrovics, J. et al. "Hybrid Modular Sensor Systems: A New Generation of Electronic Noses." Jul. 7-11, 1997; pp. ss 116-ss121 vol. 1.

* cited by examiner

*Primary Examiner*—Kaj K. Olsen
(74) *Attorney, Agent, or Firm*—Fildes & Outland, P.C.

(57) ABSTRACT

A method for analyzing a papermaking process is disclosed in which several electrochemical quantities are measured from at least one liquid flow and fingerprints according to good process situations are determined. The electrochemical measurements are carried out independently of each other using at least three electrode series, each including at least three electrodes. In addition, at least one odor measurement is used from the gases that are emitted from the liquid flow into the gas space over the free liquid surface.

9 Claims, 7 Drawing Sheets

METHOD FOR ANALYZING A PAPERMAKING PROCESS AND AN ELECTROCHEMICAL SENSOR FOR ANALYZING LIQUID

CROSS REFERENCE TO RELATED APPLICATIONS

This application is a national stage entry of international application No. PCT/FI00/00861, filed Oct. 6, 2000, which claims the benefit of Finnish application FI 20000111, filed Jan. 20, 2000 and Finnish application FI 19992158, filed Oct. 6, 1999.

TECHNICAL FIELD

The present invention relates to a method for analysing a papermaking process, in which several electrochemical quantities are measured from at least one liquid flow in the process and various fingerprints according to the process situation are defined, to which the fingerprints obtained in a normal process situation are compared and the differences creating an essential difference in the initial quantities are defined. The invention also relates to, for implementing the method, an electrochemical, i.e. polarographical/galvanostatic sensor for analysing liquid. The invention particularly relates to papermaking processes, but the study of environmental waters, for example, may also be considered.

BACKGROUND OF THE INVENTION

Neural networks, i.e. neural calculation, is used for the analysis of various processes. One known neural network model is SOM (self oriented map). Such algorithms are used to form a database from the vectors of the output variables, with the aid of various process situations. Measurement vectors, which are compared with the vectors in the database, are calculated from the measurement values obtained in the process situation. If these deviate by certain criteria from all the vectors, an attempt is made to analyse what difference or differences in the output variables caused the difference in question.

Often when applying the neural network technique, a large number of process variables are included, but the results are not satisfactory. Apparently, some of the output variables have been particularly unstable, in which case they have upset the study, and have not properly represented the process situation.

Patent publications U.S. Pat. Nos. 4,818,348; 5,830,343; 5,393,399; 5,654,497; and EP 692711 disclose some liquid analysers that use polarographic sensors. In the first publication referred to, the liquid is vaporized and the vapour is led through parallel sensors. Finnish patent application 892351 also discloses a disposal electrochemical sensor, which is intended for medical use. The generally known sensors have a narrow area of application and they are usually only able to measure a few predefined substances and their contents in a liquid. A sensor according to publication U.S. Pat. No. 5,830,343 will not remain in operating condition for long, because even individual fibres can cause a short-circuit between the electrodes of the tiny sensor.

SUMMARY OF THE INVENTION

The present invention is intended to create a new kind of method and electrochemical sensor for it, in which the method provides better and more stable results that previous solutions.

The characteristic features of the method according to the invention include analyzing a papermaking process, in which several electrochemical quantities are measured from at least one liquid flow and fingerprints according to various process situations are determined, to which the fingerprints obtained in a normal process situation are compared and the differences in the output variables created by an essential change are determined, and is characterized in that the electrochemical measurements are carried out independently of each other using at least 4–15 electrode series, each comprising at least three electrodes, one common bias-electrode for all series and, in addition, at least one odor measurement is used from the gases that are emitted from the said liquid flow into the gas space over the free liquid surface.

The characteristic features of the electrochemical sensor to be used in the method include an electrochemical, i.e. polarographic/galvanostatic sensor for analyzing a liquid, in which sensor there is a measurement cell, through which the liquid is led and in which there are several working electrodes of different material and reference-electrodes and a current-supplying counter-electrode, and a pre-amplifier to amplify a weak measurement signal, and is characterized in that the electrodes are arranged in electrode series, each series including at least a working electrode, a reference electrode and a counter-electrode, and there is a common bias-electrode for all electrode series, which is a fourth electrode in each series, and there are 4–15 electrode series, each series having a pre-amplifier with a minimized connection distance.

Electrochemical measurements provide certain voltage levels. According to the invention, what substances or compounds create the responses obtained are not, as such generally determined, though this is, as such, possible. Instead, so-called 'fingerprints' for specific process situations are obtained from the measurements. These can correspond to either good or bad situations. The scope of application of the method expands considerably if, in addition to the electrochemical measurements of the liquid flow, odor measurements are made from the gas released from the liquid flow. This is because it has been observed that the powerful effects of some compound may be easily visible from the 'odor vector', even though a relatively faint response is detected when investigating the liquid. Such odor vectors are provided by, for example, bacterial growths, extractives, or certain surfacing substances. The odor is studied from the liquid in such a way that the vapor of the liquid is allowed to be released, for example, into an air space, in which an odor sensor is located. One such odor sensor is disclosed in, for example, WO publication 97/05476. It is often advantageous to measure the odor sample at different temperatures, for example, at 50° C., 70° C., and 100° C.

Electrochemical measurements generally require the stabilization of the sample and often the use of several pairs of electrodes, but in this case this is not necessary, as long as the changes are measured and the data obtained is used in neural network calculation. The measurement cells formed by the pairs of electrodes, and generally also the pH and temperature sensors form a basic result space of the sample, to which the data from the odour measurements are added. Preferably, the electrochemical measurements are made in a multi-sensor matrix, in which the pairs of electrodes are arranged radially in relation to the input channel, in which a common bias-electrode is located. By this means, the measurements do not interfere with each other and the liquid has the same properties in each measurement. There are at least three, and preferably four electrodes in the series. There are at least three measurement cells, if an odour sensor is included, oherwise 4–15, preferably 6–10.

In the following, the invention is illustrated by reference to the accompanying figures, which show one method according to the invention and the sensor and program used in it.

DETAILED DESCRIPTION OF THE INVENTION

The measurement apparatus according to the invention comprises an intelligent on-line sensor, by means of which monitored substances that have dissolved in liquid taken from the process and changes in their contents are detected, without, however, identifying these substances. Process situation detection is based on electrochemical phenomena taking place in the working electrodes, on measurements of pH and temperature, and on artificial intelligence implemented with the aid of a computer, which exploits a predetermined database and selected additional information. This may be the plant's normal process data and/or odour measurements from the same liquid.

Figure 1:
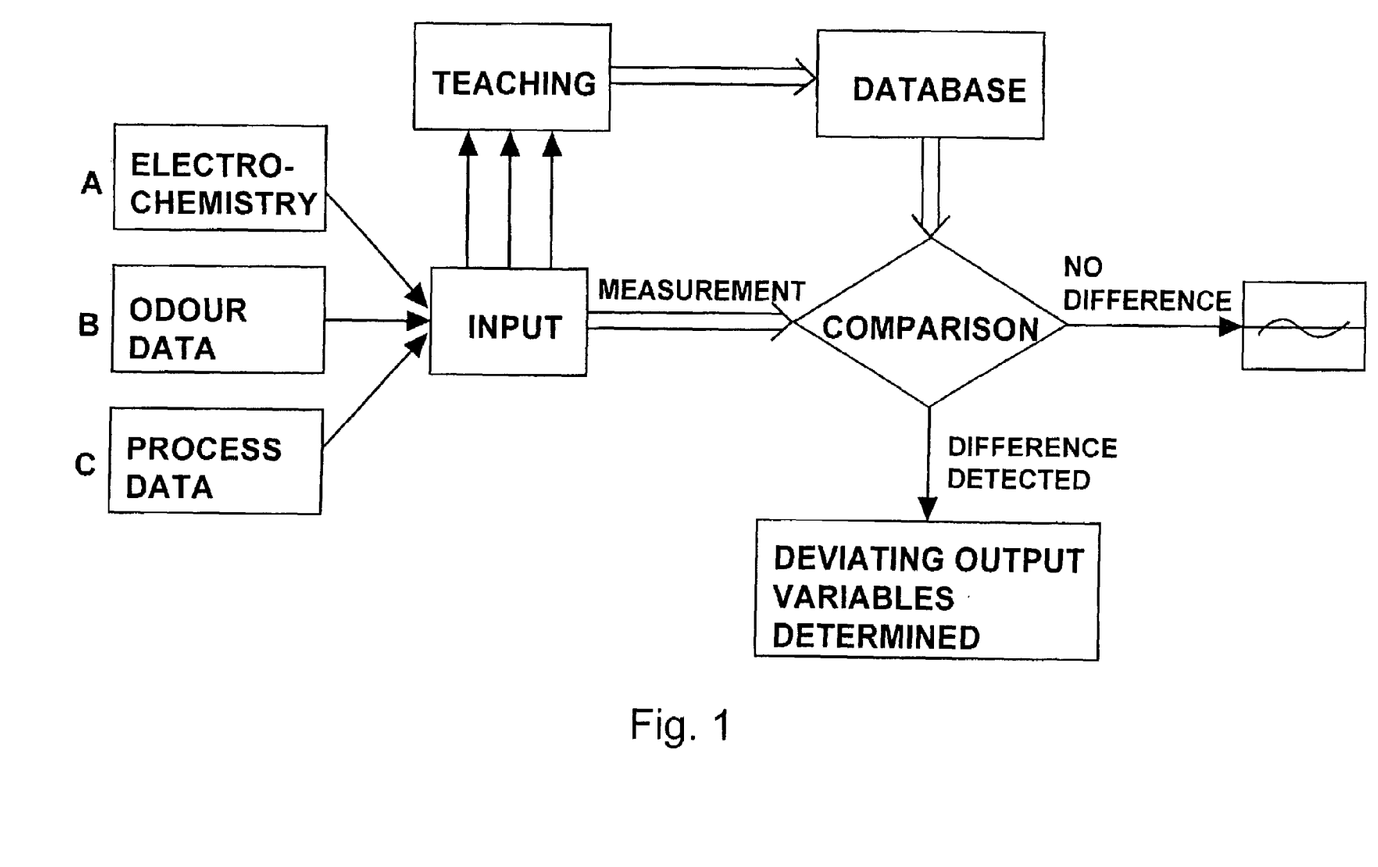
FIG. 1 shows a neural network model for analysing a process

The detection, according to FIG. 1, of process situations takes place on the bases of electrochemical, odour measurement, and process data. The selected data are entered in a neural-network program (SOM or some other neural network program), in which a directional vector is formed in multidimensional space from the measurement results and is compared with vectors, which represent good process situations, and which are in the memory of the apparatus and have been taught to the apparatus. If the vector obtained is sufficiently close to a vector in the library, it is then identified as a good process situation, otherwise a search is made for the differences in the output variables that are causing the problem.

The vector library is formed by searching for good process situations by subjecting the system to selected process situations and saving the directional vectors obtained from them in the memory of the apparatus. The apparatus's memory may contain several hundred such directional vector 'process situation identification traces' formed from these sensor signals. The selection of good process situations can naturally also take place after the event, after thorough analysis. The apparatus is preferably made to be modular, so that it can be easily adapted to different applications. The measurements sensor is a single compact package containing measurement cells and galvanically insulated electronics. The actual data processing, detection, and maintenance of the directional vector library takes place by means of a separate commercial, high-speed, powerful microprocessor card, such as the PC-104. The other elements are independent packages, which are connected to each other with the aid of a fixed flow channel.

Figure 2:
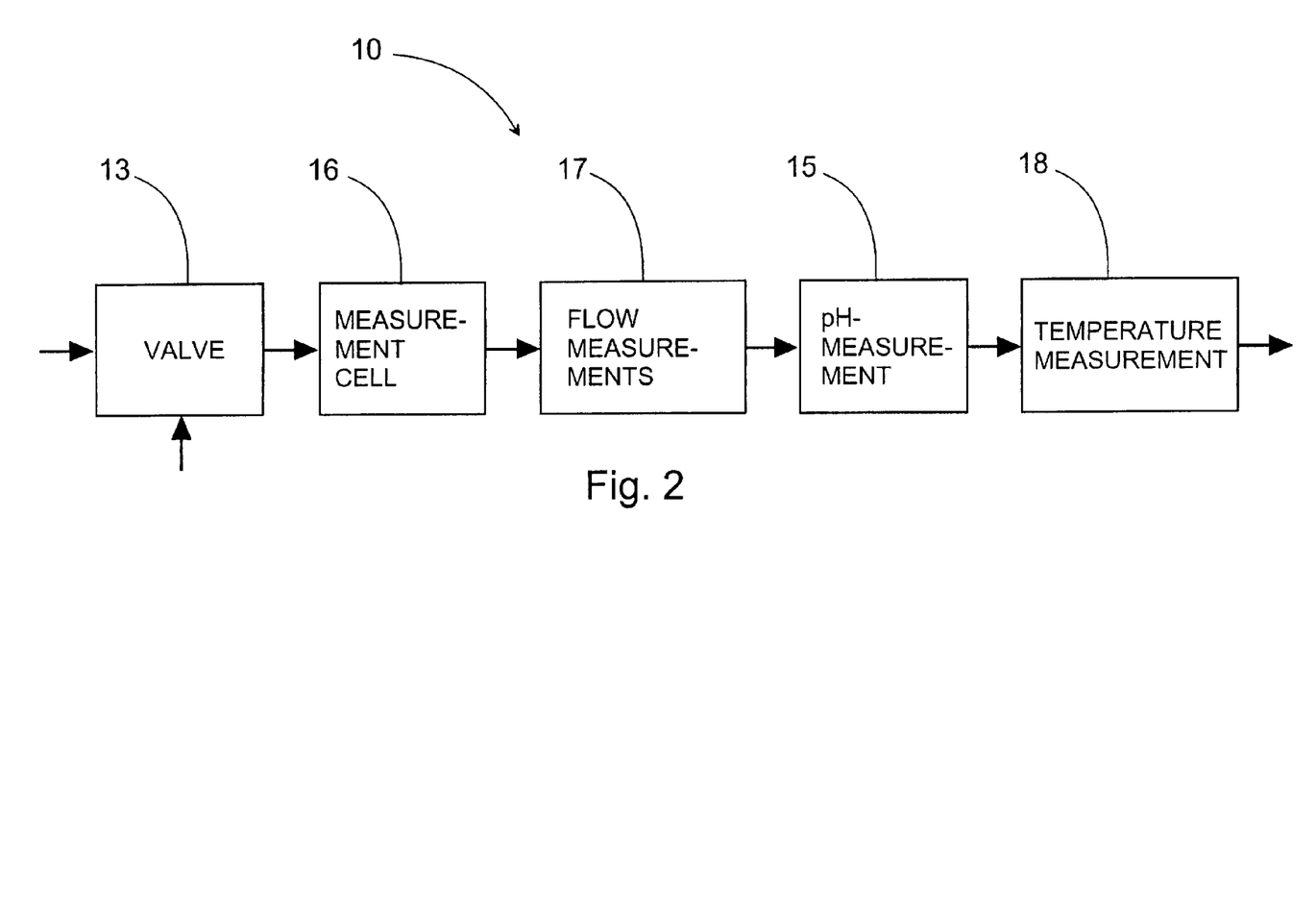
FIG. 2 shows the flow chart of an electrochemically measured liquid

According to FIG. 2, the electrochemical measurement liquid-flow circuit includes a valve 13, a sensor unit 16, flow meters 17, a pH measurement sensor 15, and temperature measurement 18.

The sample line is formed to be so spacious and flexible, that it is not even necessary to filter fibrous samples. This avoids the change in samples caused by filtering.

The actual substance detection sensor is preferably comprised of six or more measurement cells, which are located radially around a bias-electrode.

Figure 3:
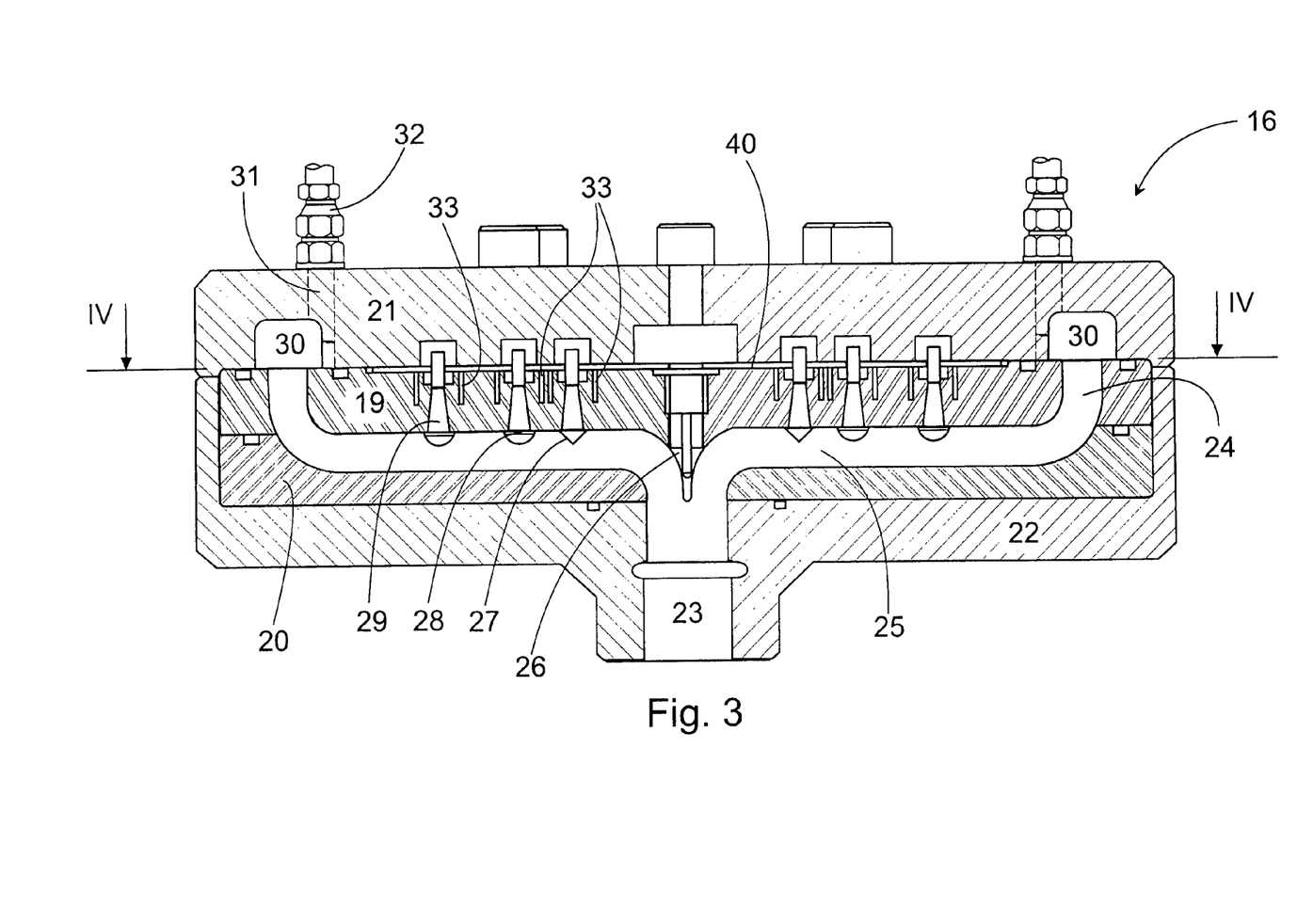
FIG. 3 shows a cross-section of a multi-detector sensor

In the arrangement according to FIG. 3, the working electrodes 27 in the measurement cell 16 are tuned to be sensitive to the substances to be investigated by using a differential amplifier to feed current through each counter-electrode 29 and a solution to the working electrode 27, until the target potentials are achieved between the working electrodes 27 and the reference electrodes 28. The amount of current is determined by the target potential, the properties of the solution, and the materials of the working electrodes. The target potentials are determined from the polarization curves run using a measurement device. Alternatively, the measurement is carried out galvanostatically, in which case the current value is set to be constant and the voltage responses are measured as the solution changes. It is advantageous to run small alternating voltage components on top of the direct-current voltage input, as this increases the reliability of the measurement.

The base level of the apparatus's measurement is set, for example, as the current-signal levels of the measurement cells, which are obtained using a pure liquid, for example, water. The base level is updated from time to time in the apparatus's memory, if its rate and degree of change are not greater than the predefined levels. When kitchen salt, for example, is added to pure water, the current-signal levels change in relation to the base level and compared to each other. The added substance and the amount of it are determined from the relative changes in the measurement signals obtained.

Each measurement cell has its own analog measurement electronics card, and the measurements relating to the diagnostics themselves. The analog card is connected by a bus to the computer of the measurement sensor.

The measurements can also be made by using only the voltage differences between the reference and working electrodes, without current input, which provides its own input space.

The software is divided into several different sub-areas: measurement of the rest potentials, running of the polarization curves, learning the substances to be detected and the disturbance substances and the actual process situation detection. The running of the polarization curves takes place by giving the measurement cell the initial and final potentials, the change potential, and the levelling time. The liquid used is a so-called pure liquid for study, for example, pure groundwater. The angle coefficient between the so-called Taffel's straight lines, which depict the concentration in the solution at any one time, can be derived from the polarization curves. Next, the run is started, when the potentiostat is given the initial potential as the target and the potentiostat runs between the reference and working electrode to the desired voltage, by feeding current through the counter-electrode and the solution to the working electrode. The potential remains in this potential value for the levelling time, after which the current is measured. Next, the potentiostat is given a new target, which is a change potential greater than the previous target value. The potential again remains at this value for the levelling time, after which the current is measured again. This procedure is continued, until the final potential is reached. A curve is plotted from the potential and current values thus obtained, from which the desired target potential can be seen. A target potential from the horizontal part of the polarization curve, in which the electrochemical reactions and thus the current signals provided by the sensor are at a minimum, is selected for each pair of electrodes.

In the teaching and detection situations, the potentiostats are set to these target potentials and the sensor's current signals obtained with these target potentials are the so-called sensor's base level, with which the changes are compared.

Figure 4:
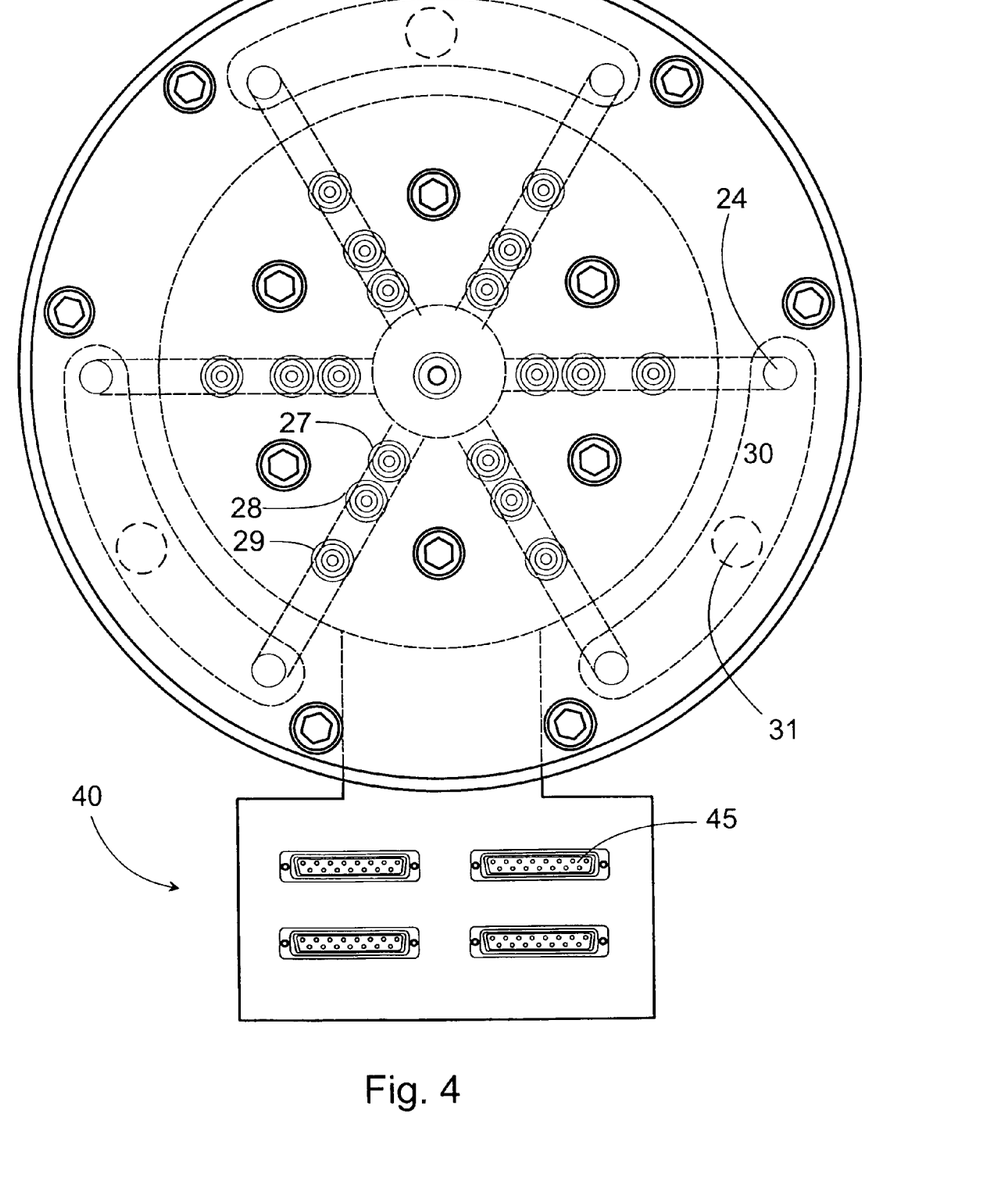
FIG. 4 shows a transverse section of the multi-detector sensor of FIG. 3 at the point IV—IV of FIG. 3
Figure 5:
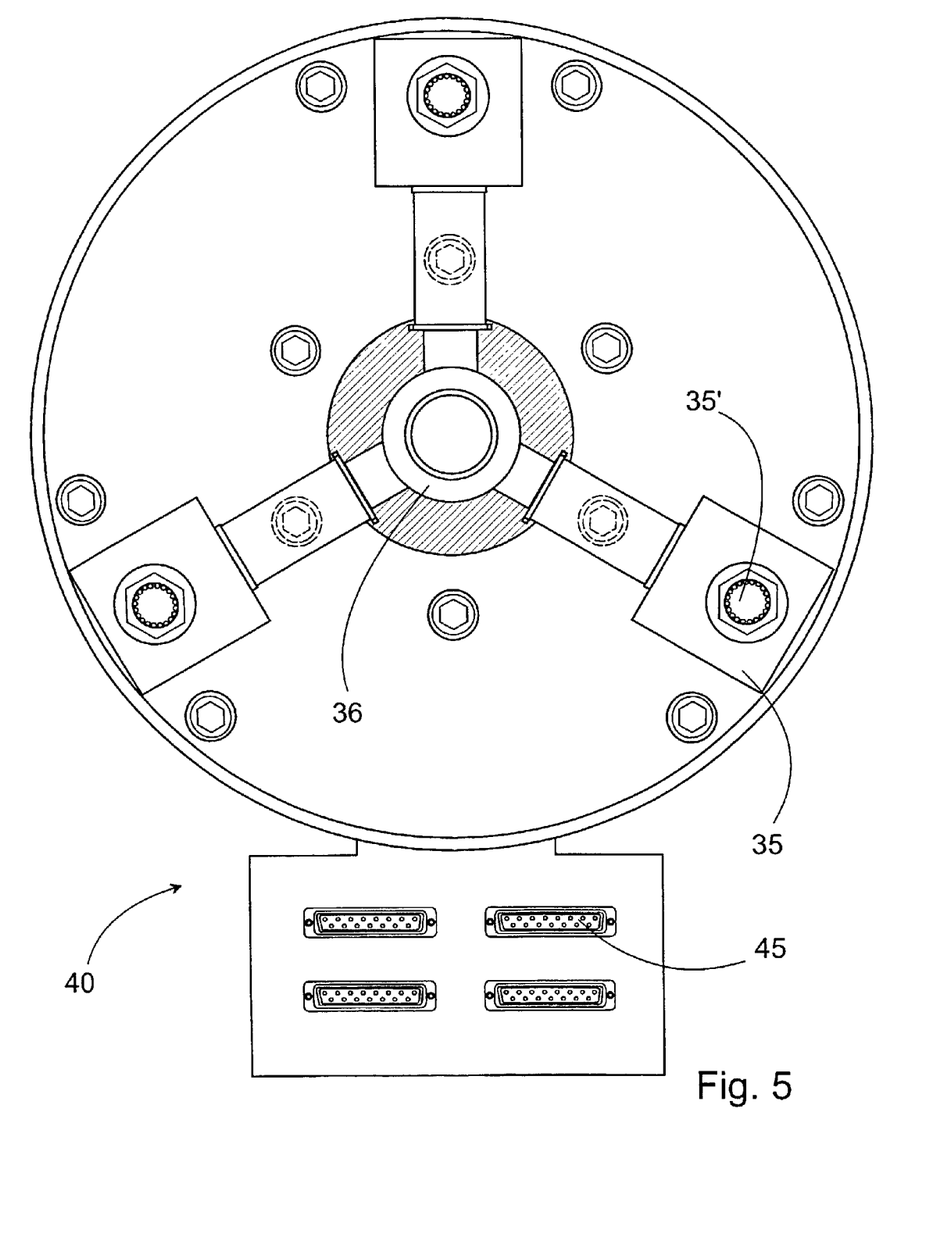
FIG. 5 shows a top view of the rotameter system of the sensor of FIG. 3

The measurement sensor 16 according to FIGS. 3 and 4 includes a base component 22, a channel plate 20, an electrode cover 19, a circuit card 40, and a cover plate 21. In base component 22, there is an intake channel 23, which, in channel plate 20, divides radially into measurement channels 25, at the ends of which are outlet channels 24 that penetrate the electrode cover. These are joined together in pairs, with the aid of intermediate channels 30, in cover plate 21, in which there are also connections 31, leading away from intermediate channels 30, and to which the rotameters that are disclosed later are connected by means of connectors 32.

Cover plate 20 and electrode cover 19 are made from Teflon. Electrodes 26, 27, 28, and 29 are attached to electrode cover 19 in such a way that one end of them extends to channel 25 and the opposite end can be connected directly to circuit card 40. The said electrodes are set radially according to the flow channels 25. The bias electrode 26 is located at the intake channel 23. It also contains a high-speed temperature sensor (PT-100).

Measurement channels 23, 25, 30 are arranged to be so spacious that even liquid with a fibre content can pass through them without causing a danger of blockage. The radial channels 25 have a diameter of 0,3–3 cm, preferably 0,7–1,3 cm, while each electrode 27–29 protrudes into the channel in such a way that the speed of flow increases substantially at it (15–35 The surface area of the electrode in the channel is about 1 cm$^2$. The fibre and filler particles keep the electrodes clean.

A protectively earthed cylinder 33, which extends to at least one-third of the depth of electrode cover 19, is arranged around electrodes 27–29 on the circuit card 40 side. This has been observed to reduce the noise level considerably.

The materials of the pairs of electrodes are selected according to the desired application. What is essential is that each pair of electrodes is separate and measures the properties of the sample in its own voltage range. The electrode materials can be, e.g. platinum, gold, silver, $Fe^{3+}$, $Fe^{2+}$, stainless steel, molybdenum, zinc, titanium, cadmium, copper, glass, electrically-conductive plastic, ceramics.

Figure 6:
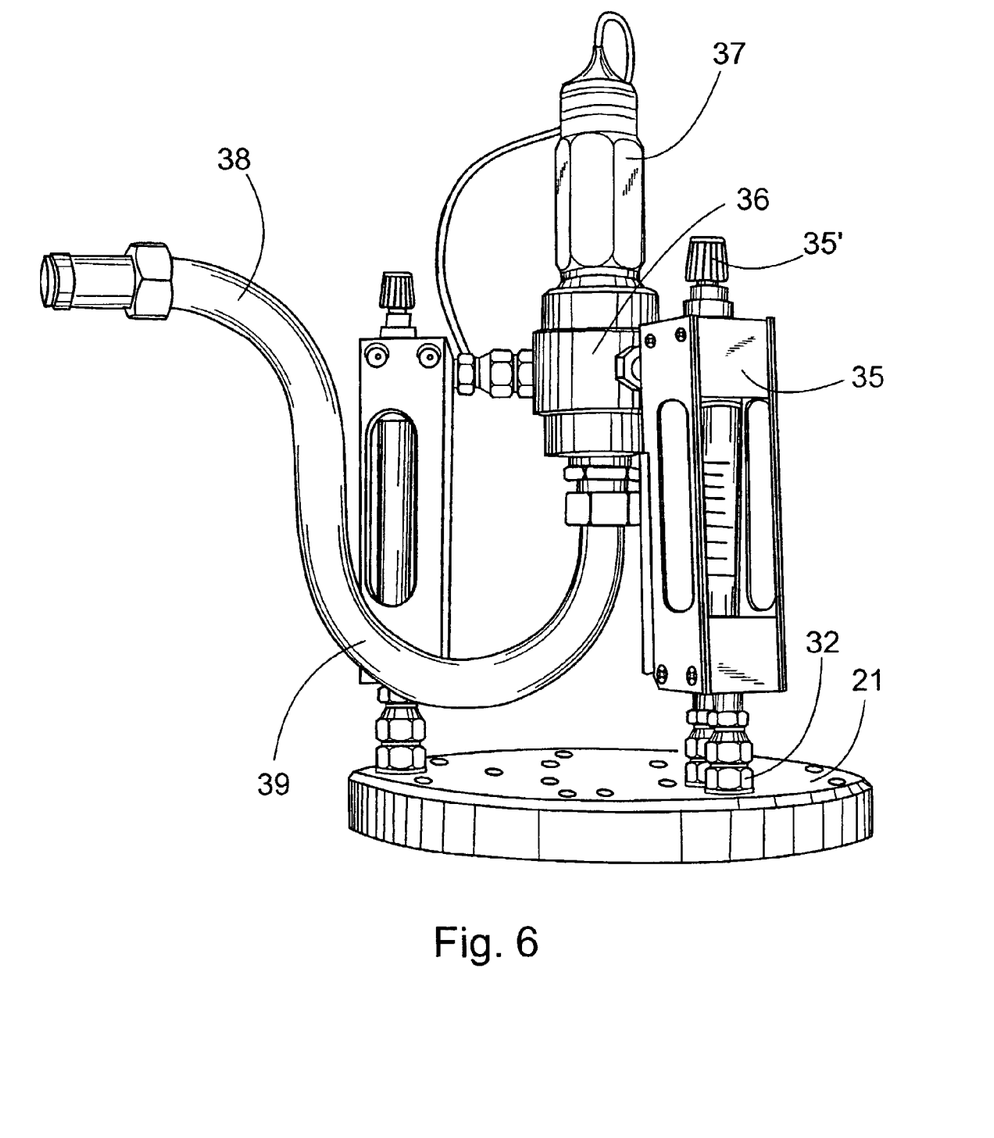
FIG. 6 shows the rotameter system of the sensor of FIG. 3
Figure 7:
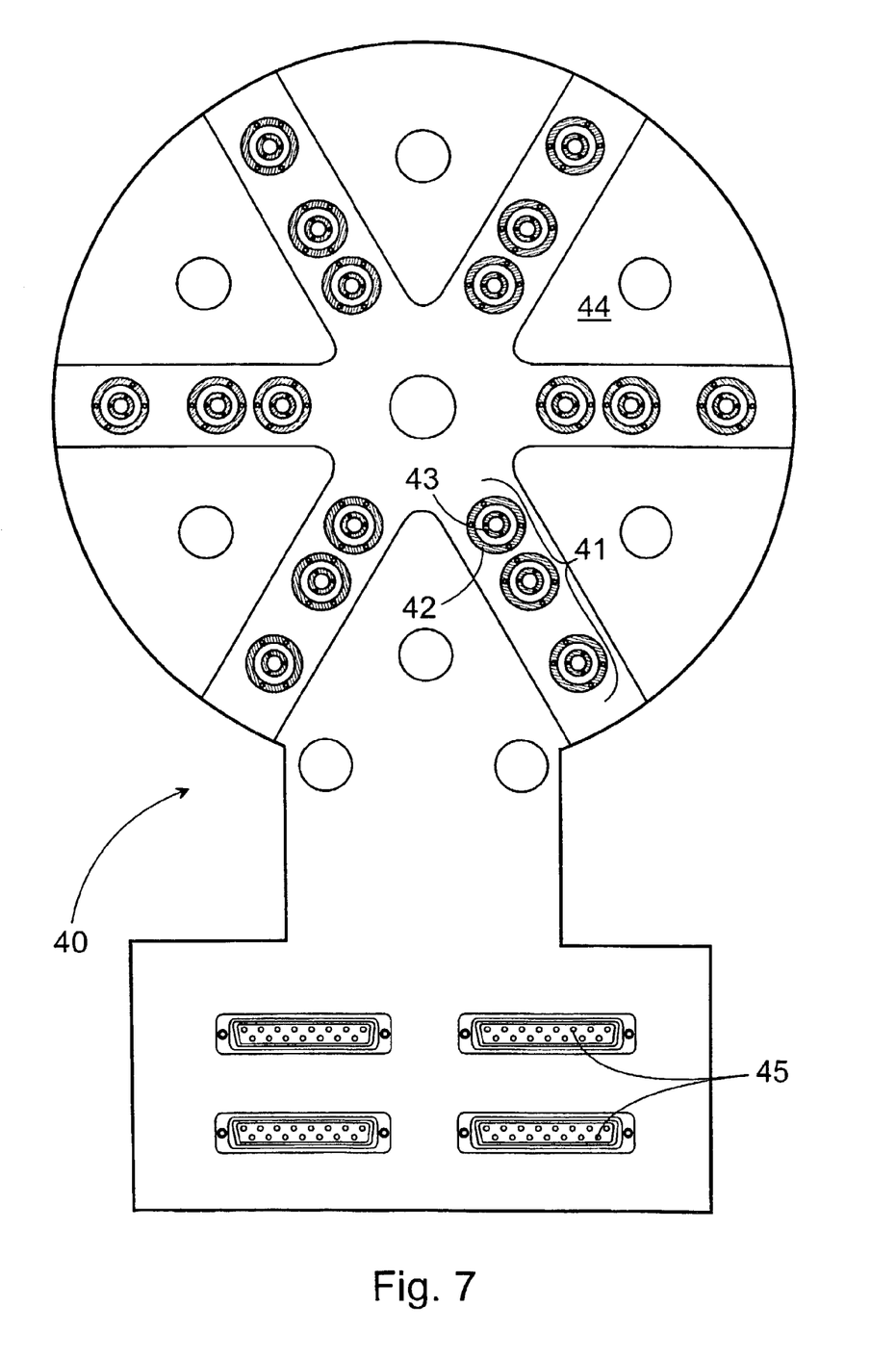
FIG. 7 shows the electronic circuit card of the multi-detector sensor

Odour data is gathered from the process liquid by allowing the gases to travel over the free surface of the liquid to a gas chamber, from where the gas is led to the odour sensors. FIGS. 6 and 7 show the exit-flow arrangement of the sensor. Flow meters 35, in this case rotameters, are connected by connectors 32 and through exit channels 31 to intermediate channels 30. Regulator valve 35' is used to adjust the flow to be equal in each line. The outlets of flow meters 35 are connected to a single distributor piece 36, inside which a sensor of pH-meter 37 is placed. A common outlet line 38 is connected to the centre of distribution piece 36.

A water trap 39, which prevents the pH-sensor from drying out during a shutdown, is connected to outlet connection 38. In the same way, liquid also remains in the measurement cell itself, preventing electrodes 26–29 from drying out.

In terms of the operation of the sensor according to the invention, it is essential that the pre-amplifiers connected to the electrodes are assembled in compact circuit card 40, FIG. 7. The electrode series are connected directly to the circuit card's connector series 41, in which there are individual conductor connectors 42 for the electrodes themselves and other conductor connectors 43 for the protective earthing. The preamplifiers are located in the space 44 between the radial series of electrodes, minimizing the connection distance. With the aid of the circuit card, the amplified measurement signals are led to the area 45 outside the sensor frame, in which there are circuits for processing the measurement signals, and output connectors.

Although the invention has been described by reference to a specific embodiment, it should be understood that numerous changes may be made within the spirit and scope of the inventive concepts described. Accordingly, it is intended that the invention not be limited to the described embodiment, but that it have the full scope defined by the language of the following claims.

The invention claimed is:

1. An electrochemical, polarographic/galvanostatic sensor for analyzing a liquid, in which sensor there is a measurement cell, through which the liquid is led and in which there are several working electrodes of different material, reference-electrodes, current-supplying counter-electrodes, and pre-amplifiers to amplify weak measurement signals, characterized in that the electrodes are arranged into 4–15 electrode series, each series including at least one of the working electrodes, one of the reference electrodes, one of the counter-electrodes, and a shared fourth electrode which is a common bias-electrode completing each electrode series, each series including one of the pre-amplifiers located proximate the electrodes of the series in a circuit card, and the electrodes being attached to an electrode cover in such a way that an end of the electrodes extends into a channel and the opposite end is connected directly to the circuit card.

2. A sensor according to claim 1, characterized in that the electrode series are placed in measurements channels branching out radially of an intake channel and said common bias electrode in the center of the intake channel.

3. A sensor according to claim 2, characterized in that the sensor includes an electrode cover covering the radial channels on at least one side, to which the electrodes are attached to extending into the said radial channels and on the other side extending to a special electronic circuit card, in which the said pre-amplifiers are installed.

4. A sensor according to claim 3, characterized in that a protectively ground cylinder, which extends over at least one-third of the depth of the electrode cover, is fitted around the electrodes on the circuit card side.

5. A sensor according to claim 2, characterized in that the radial channels have a diameter of 0.3–3 cm, and each electrode protrudes into one of the radial channels in such a way that the speed of flow increases substantially at it.

6. A sensor according to claim 2, characterized in that the common bias electrode in the center of the intake channel includes a high-speed temperature sensor.

7. A sensor according to claim 1, characterized in that the material of at least one electrode is chosen from a group consisting of platinum, gold, silver, $Fe^{3+}$, $Fe^{2+}$, stainless steel, molybdenum, zinc, titanium, cadmium, copper, glass, electrically-conductive plastic, and ceramics.

8. A sensor according to claim 1, characterized in that the pre-amplifier connected to each series is located in the space between the electrode series in the immediate vicinity of each electrode series.

9. A sensor according to claims 1, characterized in that the electrode series are arranged in such a way that liquid remains around the electrodes during a shutdown.

* * * * *